United States Patent [19]

Sugimori et al.

[11] Patent Number: 5,116,752
[45] Date of Patent: May 26, 1992

[54] PROCESS FOR PREPARING NEURAMINIDASE

[75] Inventors: Tsunetake Sugimori, Uji; Yoji Tsukada, Kyoto; Yasuhiro Ohta, Uji, all of Japan

[73] Assignee: Marukin Shoyu Co., Ltd., Kagawa, Japan

[21] Appl. No.: 640,548

[22] Filed: Jan. 15, 1991

Related U.S. Application Data

[63] Continuation of Ser. No. 171,869, filed as PCT/JP87/00386, Jun. 12, 1987, abandoned.

[30] Foreign Application Priority Data

Jun. 16, 1986 [JP] Japan .................. 61-139896

[51] Int. Cl.$^5$ .................. C12N 9/24; C12N 1/20
[52] U.S. Cl. .................. 435/200; 435/252.1; 435/830
[58] Field of Search .......... 435/200, 830, 172.1, 435/252.1

[56] References Cited

U.S. PATENT DOCUMENTS

| 4,071,408 | 1/1978 | Flashner et al. | 195/62 |
| 4,699,883 | 10/1987 | Sugimori et al. | 435/232 |
| 4,710,470 | 12/1987 | Uwajima et al. | 435/200 |

OTHER PUBLICATIONS

Unexamined Japanese Patent Publication (Kokai) No. 51-32786 published in Japan on Mar. 19, 1976.
Journal of Bacteriology, vol. 151, No. 3, (1982), pp. 1630-1632, M. Flanner et al.—published Sep. 1982.
Chemical Abstracts, vol. 94, No. 15, Apr. 13, 1981, p. 348, Abstract No. 117509e.

Primary Examiner—Charles L. Patterson
Attorney, Agent, or Firm—Larson and Taylor

[57] ABSTRACT

The present invention provides a process for preparing neuraminidase comprising incubating a mutant of the genus Arthrobacter capable of producing neuraminidase in the absence of any inducing substance, and recovering neuraminidase from the resulting culture.

2 Claims, No Drawings

PROCESS FOR PREPARING NEURAMINIDASE

This application is a continuation of application Ser. No. 171,869 filed Feb. 8, 1988, now abandoned.

TECHNICAL FIELD

This invention relates to a process for producing neuraminidase, particularly to a process for producing neuraminidase by culturing a novel mutant strain capable of producing neuraminidase in the absence of any inducing substances.

PRIOR ART

Neuraminidase, which is also called sialidase, is an enzyme classified with the enzyme number EC. 3.2.1.18 of the Nomenclature Committee of the International Union of Biochemistry, and systematically named N-acetylneuraminate glycohydrase. This enzyme acts on various sialic acid-containing glycoconjugates and the like which are important components of organisms and causes elimination and release of the sialic acid.

Heretofore, the main sources of the above neuraminidase were pathogenic bacteria such as *Vibrio cholerae, Clostridium perfringens, Diplococcus pneumoniae, Corynebacterium diphtheriae* and the like. Our research has already led to techniques for producing the above enzyme on an industrial scale from non-pathogenic bacteria of the genus Arthrobacter and several other genera without entailing a danger of infection (see Japanese Examined Patent Publication No. 50-11991, Japanese Patent No. 801089 and Japanese Examined Patent Publication No.52-39917, Japanese Patent No. 914556).

With the above techniques established by the present inventors, however, it is required that an inducing substance such as colominic acid or the like be present in a culture medium, and in the absence of such inducing substance, the desired enzyme can in no way be produced on an industrial scale. In other words, the microorganisms used for the above established techniques are substantially incapable of producing neuraminidase in the absence of an inducing substance such as colominic acid or the like. Furthermore, colominic acid and the like usually needs a cumbersome procedure for preparation and are expensive and are not easily available, hence disadvantageous.

DISCLOSURE OF THE INVENTION

An object of the present invention is to provide a technique which can obviate the greatest drawback of the foregoing techniques that they essentially require the use of an inducing substance such as colominic acid or the like, and which is capable of producing a large amount of neuraminidase on an industrial scale without necessitating the use of colominic acid or the like.

The present inventors have conducted intensive research to accomplish the above object. Consequently, we have found the fact that, among the mutants obtained by subjecting the microorganisms of the genus Arthrobacter used for the above prior techniques to a mutation treatment, there exist certain microorganisms which are capable of producing a large quantity of the desired enzyme in a culture medium that is free from an inducing substance such as colominic acid or the like, i.e., the fact that the above mutation treatment creates mutant microorganisms capable of producing neuraminidase in the absence of an inducing substance. We found the fact that the above object is accomplished by culturing said mutant microorganism. This invention has been accomplished based on this novel finding.

This invention provides a process for producing neuraminidase comprising culturing a mutant of the genus Arthrobacter capable of producing neuraminidase in the absence of any inducing substance, and collecting neuraminidase from the resulting culture.

This invention also provides a mutant of the genus Arthrobacter capable of producing neuraminidase upon incubation in a nutrient medium containing sources of carbon and nitrogen and inorganic substance but free of any inducing substance, or a biologically pure culture of said mutant.

In this specification, inducing substance refers to a substance which, when added to the culture medium in which the bacteria of the genus Arthrobacter or other bacteria used in the prior techniques are incubated, endows these bacteria with the ability of producing neuraminidase. Such inducing substance includes colominic acid and related compounds thereof such as sialic acid, ganglioside wherein sialic acid is contained as bonded, sialomucopolysaccharide and the like or decomposition products of sialic acid, such as mannosamine, N-acetylmannosamine and the like.

According to the present invention, the use of the above mutant strains obviates the use of an inducing substance such as colominic acid or the like which needs cumbersome procedure to prepare, is expensive and entails disadvantages, and it is now possible to produce and accumulate a large quantity of neuraminidase in a culture medium which is used for the incubation of usual microorganisms. Thus according to the present invention the enzyme can be produced easily and in a large amount on an industrial scale.

With the process of the present invention, it is important to use mutants of the genus Arthrobacter. Such mutants can be prepared from known bacteria of the genus Arthrobacter as parental strain by application of conventionally used means for mutation treatment. As the parental strains, any strains of the genus Arthrobacter capable of producing neuraminidase in the presence of an inducing substance can be used. Examples thereof are *Arthrobacter ureafaciens* ATCC 7562, *Arthrobacter aurescens* ATCC 13344, *Arthrobacter oxydans* ATCC 14358 and the like.

Examples of useful means for mutation are a variety of those widely known and include chemical mutagenic agents such as nitrosoguanidine (namely N-methyl-N'-nitro-N-nitrosoguanidine), Mitomycin C, 4-nitroquinoline-1-oxide, methyl methanesulfonate, ethyl methanesulfonate, ethyl ethanesulfonate, 2-aminopurine, 5-bromouracil, nitrous acid, hydroxylamine, acriflavine, acridine mustard and the like, radiation such as X-ray irradiation, ultraviolet irradiation, etc. These means can be used singly or in a suitable combination. These means for mutation can be applied in a conventional manner. For example, as to the chemical mutagenic agents, the concentrations and duration of treatment are suitably determined in accordance with the conventional technique used for each of the mutagenic agents. Typically, N-methyl-N'-nitro-N-nitrosoguanidine is used at a concentration of about 50 to about 200 $\mu$g/ml for about 0.5 to about 1 hour; ethyl methanesulfonate is used at a concentration of about 0.01 to about 0.5 M for about 0.5 to about 12 hours; 2-aminopurine is used at a concentration of about 100 to about 500 $\mu$g/ml for about 3 to about 24 hours; 5-bromourcil is used at a concentration of about 20 to about 100 $\mu$g/ml for about 1 to about 12 hours; acriflavin is used at a concentration of about 1 to 100 μg/ml for about 0.5 to about 12 hours. The concentration of other mutagenic agents and the duration for the treatment are within the knowledge of the art and suitably determined. Ultraviolet irradiation is preferably conducted by irradiating the medium for about 10 seconds to about 3 minutes with use of a mercury lamp of 10 to 15 w placed 10 to 70 cm above the medium. The amount of X-ray to be irradiated is about 10,000 to about 100,000 Roentgen.

Especially preferable examples of the above mutant to be used in the present invention is *Arthrobacter ureafaciens* M1057 which is obtained from *Arthrobacter ureafaciens* ATCC7562 as a parent strain by treatment with chemical mutagenic agent.

The method of preparing the contemplated mutant is illustrated below by citing *Arthrobacter ureafaciens* M1057 as an instance.

The strain M1057 is prepared as follows. A loopful of the above parent strain is first inoculated into L medium containing 1.0% (% by weight, the same hereinafter) of peptone, 0.5% of yeast extract and 0.1% of glucose and adjusted to a pH of about 7.2. The medium was incubated at 30° C. with shaking. The bacteria are harvested at the mid-phase of logarithmic growth, washed with physiological saline, and then suspended in physiological saline so as to prepare a cell suspension having a concentration of about $5 \times 10^8$ cells/ml. Into the suspension thus prepared, nitrosoguanidine is added to a final concentration of about 50 to 200 μg/ml, and the mixture is incubated at about 30° C. for about 30 to about 120 minutes with mild shaking. The bacteria are collected by centrifugation, washed with physiological saline, and suspended in physiological saline. A portion of the suspension is spread onto a usual culture medium such as a solid medium comprising 0.5% of peptone, 0.5% of yeast extract and 2.0% of agar (hereinafter referred to as "YPA medium"). This is incubated at about 30° C. to form colonies. Each colony formed is transferred to a medium (YP medium) which is the YPA medium free of agar, and further incubated overnight at about 30° C. with shaking. After the culture solution thus obtained is subjected to centrifugation, the neuraminidase activity of the supernatant is determined by a conventional method to select a strain having marked productivity of the contemplated enzyme.

Thus, the strain M1057 is obtained as one of the selected strains. This strain distinctly differs from the parent strain in that the former has ability of producing remarkable amount of neuraminidase in the absence of an inducing substance. Except this feature, the strain has the same mycological characteristics as the parent strain. Thus the strain is identified as a mutant of the genus Arthrobacter.

The above strain M1057 was deposited on June 11, 1986 as *Arthrobacter ureafaciens* M1057 with the number FERM P-8804 at the Fermentation Research Institute, Agency of Industrial Science and Technology, Ministry of International Trade and Industry, 1-3, Higashi 1-chome, Yatabe-machi, Tsukuba-gun, Ibaraki-ken, Japan, and the deposit was covered to a deposit under the Budapest Treaty on June 5, 1987, and assigned a number FERM BP-1391.

Our research has revealed that not only the above parent strain (*A. ureafaciens* ATCC 7562), but also the microorganisms useful for the process previously established by us, i.e., those of the genus Arthrobacter which are capable of producing neuraminidase in a medium containing an inducing substance, when treated with nitrosoguanidine as above, can similarly be reproducibly mutated into the mutants having ability of producing a remarkable amount of neuraminidase in a medium free from an inducing substance. Further, from said various microorganisms including the above *Arthrobacter ureafaciens* ATCC 7562 as parent strains, mutants having comparable neuraminidase production ability can similarly be derived reproducibly by employing the foregoing means for mutation by chemical mutagenetic agents and/or irradiation method of radiation such as X-ray or UV irradiation in place of the above nitrosoguanidine.

These facts appear to indicate that the above microorganisms have latent ability to produce neuraminidase, which, although usually remaining undeveloped, is expressed manifestly upon activation by the above mutation treatment. At any rate, none of the microorganisms of the genus Arthrobacter has been known to have such remarkably improved enzyme productivity, nor is it in any way known that known microorganisms of the genus Arthrobacter can be made to express such enzyme productivity upon mutation treatment.

The process of the present invention can be carried out by incubating the mutant of the genus Arthrobacter obtained in the above manner.

This incubation can be practiced by employing either conventional liquid or solid media, but it is generally advantageous to use a liquid medium. Incubation with shaking or incubation with aeration and stirring is preferably conducted in order to produce a large amount of the desired enzyme. The media for the above incubation are not specifically limited, and various media which are commonly used for incubating microorganisms and which contain nutrients, etc. may be used. Examples of the nutrients are carbon sources including sugars such as glucose, fructose, lactose, invert sugar, saccharified starch, sorbitol and glycerol and organic acids such as pyruvic acid, malic acid and succinic acid, etc; nitrogen sources including peptides, meat extract, yeast extract, casamino acid, urea, ammonium salt, nitrate salt, etc; and so on. To the medium can be also added, for example, inorganic salts of phosphorus, magnesium, potassium, sodium, etc., a trace amount of elements such as boron, copper, iodine, iron, manganese, zinc, cobalt, molybdenum, and a trace amount of growth factors such as yeast extract and vitamins, and the like. Further usable as the above media are, for example, natural or semi-synthetic media containing extract or exudate of animal tissues. Examples of these natural or semi-synthetic media are those marketed under the name of Todd Hewitt Broth medium, Brain Heart Infusion medium, etc.

As the conditions under which the mutants are incubated in the above various media, the incubation temperature is about 20° to about 40° C., preferably about 25° to about 30° C. The neuraminidase activity reaches maximum about 15 to about 70 hours after incubation. Therefore, it is advantageous that the incubation is stopped at this stage, and that the desired neuraminidase is collected from the culture. This collection of the contemplated enzyme from the culture can be conducted by a common methods, e.g., by removing the bacteria from the culture solution and subjecting the supernatant to purification such as salting-out with ammonium sulfate, column chromatography and the like. Thus purified neuraminidase can be obtained.

EXAMPLES

The present invention will be described in greater detail with reference to the following examples.

The neuraminidase activity in each example is determined according to the following method. A total 0.2 ml quantity of a solution consisting of 0.1 ml of a sample enzyme solution, 0.05 ml of 0.4% solution of N-acetylneuraminosyl lactose (product of Boehringer-Mannheim-YAMANOUCHI) and 0.05 ml of 0.2M acetic acid buffer (pH 5.0) was subjected to reaction at 37° C for 10 minutes, and the amount of released N-acetylneuraminic acid (sialic acid) was determined according to the thiobarbituric acid method (L. Warren, J. Biol. Chem., 234, 1971 (1959)).

One unit of neuraminidase activity is defined as the activity wherein the enzyme solution releases one micromole of N-acetylneuraminic acid under the above reaction conditions per minute.

EXAMPLE 1

Into a 500-ml Erlenmeyer flask were placed 0.5 g of lactose, 0.2 g of diammonium hydrogen phosphate, 0.3 g of sodium chloride, 0.1 g of dipotassium hydrogen phosphate, 0.01 g of magnesium sulfate and 100 ml of water. The mixture was adjusted to a pH of 7.0 and then sterilized by heating to prepare a culture solution.

The above culture solution was innoculated with *Arthrobacter ureafaciens* M1057 (FERM P-8804), and incubated with shaking at 28° C. for 24 hours, giving 105 ml of culture filtrate.

The neuraminidase activity per ml of the crude enzyme solution obtained was 2.8 units.

Subsequently, 100 ml of the culture filtrate obtained as above was subjected to salting-out with ammonium sulfate, and a fraction of 30 to 90% saturation (as expressed by the Osborne method) was dissolved in a small amount of water followed by dialysis against 10 mM acetic acid buffer (pH 4.5).

Soluble starch and colominic acid were dissolved in 2N sodium hydroxide, and epichlorohydrin was added thereto to prepare a gel having the colominic acid as a ligand. The dialysate was passed through the column packed with the gel for adsorption. Elution with 100 mM acetic acid buffer (pH 4.5) gave 273.8 units of purified neuraminidase (yield: 97.8%).

It was found that the purified neuraminidase thus obtained did not contain protease, N-acetylneuraminic acid aldolase, phospholipase C and glycosidases.

COMPARISON EXAMPLE 1

Using the parent strain *Arthrobacter ureafaciens* ATCC 7562 in place of the mutant M1057 and conducting incubation in the same manner as in Example 1, the resulting enzyme activity was determined. The enzyme activity per ml of the culture solution was found to be 0.002 unit.

It should be noted that the parent strain gave a culture solution which exhibited an enzyme activity of 3.2 units per ml of the culture solution, when incubated in the medium containing colominic acid, which consisted of 0.5 g of colominic acid, 0.2 g of diammonium hydrogen phosphate, 0.3 g of sodium chloride, 0.1 g of dipotassium hydrogen phosphate, 0.01 g of magnesium sulfate and 100 of water and which was adjusted to a pH of 7.0 and sterilized by heating.

EXAMPLE 2

Into a 500-ml Erlenmeyer flask were placed 1.0 g of peptone, 0.5% yeast extract, 0.5% sodium chloride and 100ml of water. The mixture was adjusted to a pH of 6.5 with sodium hydroxide and then sterilized by heating to prepare a culture solution. The medium was innoculated with the same *Arthrobacter ureafaciens* M1057 as that used in Example 1, and the inoculum was incubated with shaking at 30° C. for 24 hours. The culture filtrate obtained was used as a crude enzyme solution.

The neuraminidase activity per ml of the solution was 3.0 units.

The dialysate thereof was subjected to adsorption by affinity column and elution was conducted in the same manner as in Example 1, giving.292.2 units of neuraminidase (yield: 97.4%). No contaminating enzymes were observed as in Example 1.

We claim:

1. A process for preparing neuraminidase comprising culturing *Arthrobacter ureafaciens* M 1057 under conditions suitable for production of meuraminidase, and recovering neuraminidase from the resulting culture.

2. A biologically pure culture of *Arthrobacter ureafaciens* M1057.